United States Patent [19]

Andersen

[11] Patent Number: 5,135,715
[45] Date of Patent: Aug. 4, 1992

[54] METHOD OF MAINTAINING RELATIVE HUMIDITY IN GAS STERILIZERS

[75] Inventor: Harold W. Andersen, Oyster Bay, N.Y.

[73] Assignee: H. W. Andersen Products, Inc., Oyster Bay, N.Y.

[21] Appl. No.: 754,817

[22] Filed: Sep. 4, 1991

Related U.S. Application Data

[62] Division of Ser. No. 416,896, Oct. 4, 1989, Pat. No. 5,082,636.

[51] Int. Cl.$^5$ .............................................. A61L 2/00
[52] U.S. Cl. ........................................ 422/28; 422/34; 422/40; 422/1; 239/56; 53/432; 53/434
[58] Field of Search .................. 422/1, 4, 34, 40, 294, 422/28; 53/432, 434, 474; 239/55, 56

[56] References Cited

U.S. PATENT DOCUMENTS

| | | | |
|---|---|---|---|
| 1,637,814 | 8/1927 | Gallagher | 239/55 |
| 3,476,506 | 11/1969 | Andersen et al. | 422/34 |
| 3,630,665 | 12/1971 | Andersen et al. | 422/34 |
| 3,716,961 | 2/1973 | Cope et al. | 422/34 |
| 3,815,315 | 6/1974 | Glick | |
| 4,066,399 | 1/1978 | Gunther | 422/27 |
| 4,590,037 | 5/1986 | Kaye | 422/116 |
| 4,937,046 | 6/1990 | Andersen et al. | 422/34 |

*Primary Examiner*—Robert J. Warden
*Assistant Examiner*—Theresa A. Trembley
*Attorney, Agent, or Firm*—Jordan and Hamburg

[57] ABSTRACT

A method for maintaining hydration of the contents of water-impermeable packages containing items to be sterilized includes placing a moisture-releasing humidifying device into the package with the items to be sterilized, hermetically sealing the package, and releasing moisture from the moisture-releasing humidifying device into the package before the package is exposed to the gaseous sterilant. The moisture-releasing humidifying device includes an absorbent material and a cover about the absorbent material. The cover is made at least partially of a hydrophobic and vapor-permeable material such that moisture absorbed by the absorbent material passes through the vapor-permeable material to effect humidification within the package.

11 Claims, 4 Drawing Sheets

METHOD OF MAINTAINING RELATIVE HUMIDITY IN GAS STERILIZERS

This is a division of application Ser. No. 07/416,896, filed Oct. 4, 1989 now U.S. Pat. No. 5,982,636.

BACKGROUND OF THE INVENTION

The present invention relates to a method and to a humidifying device for assuring the maintenance of hydration of the contents of water impermeable packages or bags containing instruments and supplies to be sterilized by gas sterilization processes regardless of the ambient relative humidity of the environment surrounding the water impermeable packages or bags.

It has been widely recognized for many years by those skilled in the art and science of sterilization with gases such as ethylene oxide that the sterilization gas is more effective in killing microorganisms if those microorganisms are normally hydrated and, further, if the sterilization process is carried out in an atmosphere which contains at least 30% relative humidity. However, chamber-type ethylene oxide sterilizers, for example, heat their contents at the beginning of the sterilization cycle, thereby sharply reducing the relative humidity of the atmosphere in the chamber. To compensate for this, steam is injected into the chamber at the beginning of the sterilization cycle in an attempt to rehydrate dehydrated organisms and increase the hydration of the contents of the chamber prior to the introduction of the sterilizing gas. Provided that the contents of the chamber are packaged in water-permeable wrappings and enough water is introduced, this is a successful system.

However, when items to be sterilized are packaged in gas-permeable but water-impermeable wrappings, for instance, sealed in individual water-impermeable plastic bags, the contents of such packages will not be rehydrated by the injection of steam into the chamber and will be exposed to sharply declining relative humidity as the temperature of the chamber increases. Typically, relative humidity will decline by 50% for every 10° C. rise in temperature.

The present invention relates to a method of assuring the maintenance of hydration of the contents of water-impermeable packages containing instruments and supplies during the gas sterilization process regardless of the ambient relative humidity. It further discloses the particular advantages of the invention as it pertains to gas diffusion-type gas sterilizers, for example, of the type marketed by H. W. Andersen Products, Inc. under the registered trademarks ANPROLENE ® and STERIJET ®.

In the aforementioned gas diffusion-type gas sterilizers, items to be gas-sterilized are generally individually packaged in gas-permeable wrappings or packages The user depends on these wrappings or packages to maintain the sterility of the items between the time they are removed from the sterilizer up to the time they are used. This often means that the wrappings or package must prevent the recontamination of its contents for years and through multiple shipments and rough handling. Water impermeable plastic films have proven to have many of the desirable features for use as the wrapping or packaging material for the above gas diffusion-type sterilizers.

More specifically, a prior art ethylene oxide gas sterilizer of this type is shown in FIGS. 1 to 3, wherein items to be sterilized are disassembled, washed, toweldried and wrapped in a wrapping material such as cloth, paper or a plastic wrapping such as a proprietary plastic wrapping sold by H. W. Andersen Products, Inc. under the trademark SEAL AND PEEL ®. The wrapped items to be sterilized are identified by the numeral 12, and these wrapped items 12 are placed in a gas diffusion membrane in the form of a water impermeable plastic bag 14 which is referred to as a liner bag 14. As shown in FIGS. 2 and 3, a gas-release mechanism 16 consists of liquid ethylene oxide sealed inside of a glass ampule 18 and packaged inside of a hermetically sealed gas diffusion membrane in the form of a plastic gas release bag 20 The system is activated by snapping a prescored neck 22 of the ampule 18 without puncturing the gas release bag 20 surrounding it This is achieved by placing ampule 18 in a protection sleeve 24 in membrane 20. After activation, the activated gas-release bag 16 is placed with the wrapped items 12 to be sterilized inside of the liner bag 14. The liner bag 14 is hermetically sealed around its contents (the wrapped items 12 to be sterilized and the activated gas-release bag 16) by means of a simple wire tie 26. The liner bag 14 is further enclosed in a ventilated container 28. During the sterilization cycle, which occurs at ambient room temperature, the liquid ethylene oxide in the sealed gas-release bag 20 boils, converting to pure ethylene oxide gas. The gas diffuses through the walls of the gas-release bag 20 and mixes with the air in the liner bag 14 in sufficient concentration to penetrate and sterilize the wrapped items 12. As the concentration of the gas increases in the liner bag 14, the ethylene oxide further diffuses through its walls into the surrounding container 28 from whence it is ventilated to the outside atmosphere. This gas sterilization system is marketed commercially by H. W. Andersen Products, Inc. under the registered trademark ANPROLENE ® and is disclosed in U.S. Pat. No. 3,476,506, the entire contents of which are incorporated herein by reference.

Inasmuch as the liner bag 14 of such a system is substantially impermeable to water vapor, the relative humidity of the air in the liner bag 14 at the beginning of the sterilization cycle is maintained throughout the normal 12-hour exposure period If the items to be sterilized have been washed with detergent and water as required, no dehydrated and hence no resistant microorganisms will be present. Effective use of the system, however, thus requires a minimum ambient relative humidity in the room where sterilization is performed. Present practice is to warn the user of such a sterilization system to measure the relative humidity in the room at the beginning of the sterilization cycle and not to proceed unless the relative humidity is at least 30% This presents obvious limitations and disadvantageous considerations in the use of such a gas sterilization system.

Another prior art gas sterilizer, marketed commercially by H. W. Andersen Products, Inc. under the registered trademark STERIJET ®, is shown, for example, in FIGS. 4 and 5, where items to be sterilized 30 are prepared by washing and drying in the same manner as for the previously-described sterilization system. These items 30 are then wrapped in paper or cloth 31 and placed in an appropriate size liner bag 32. The liner bag 32 is placed over a spout 34 extending between jaws 36, 37 of a sterilizing device so that the spout 34 extends into the bag 32 and the lips 38 of the bag 32 extend between the jaws 36, 37. The jaw 36 is mounted on a pivotal arm assembly 27. A cycle number button coinciding with the number printed on the liner bag 32 is depressed to select the appropriate dose of gas, and a foot switch is pressed to start the cycle. Rubber-cushioned jaws 36, 37 close to hermetically seal the lips 38 of the bag 32 about the spout 34. Air is pumped from the bag 32 until the bag appears to be vacuum-tight around the enclosed items 30. An appropriate dose of gas is then injected into the bag 32 through the spout 34 via the conduit 35.

After the introduction of sterilant, the arm assembly 27 is pivoted clockwise slightly to close outer jaws 44, 46 on the portion of the bag 32 therebetween. The inner, Jaws 36, 37 do not prevent the closing of the outer Jaws 44, 46 because the inner jaws 36, 37 are made of resilient material which can be compressed as the outer jaws 44, 46 are moved from the FIG. 4 position to a closed position shown in FIG. 5.

After closure of the outer jaws 44, 46, an impulse of electric current is passed through a resistance wire 42 imbedded in or just below the surface of lo 46. The upper jaw 44, which may be made of heat resistant rubber, presses the bag down against the heating wire 42. The wire 42 rapidly heats to a temperature sufficient to fuse the bag but below the ignition temperature of the sterilant thereby forming a seal in the conventional manner of heat sealing. After a short pause, to assure that the seal is cooled, the jaws 36, 37 and 44, 46 open, releasing the bag 32.

The bag 32 containing the items 30 to be sterilized and the sterilizing gas is then placed in a heated and ventilated aerator where it remains for at least 12 hours. By way of example, the aerator may be heated to 50° C. During this time, the gas sterilizes the contents of the bag 32 and then diffuses through the wall of the liner bag 32 and is evacuated by the ventilator. Since the material from which the bag 32 is fabricated is permeable to ethylene oxide and impermeable to air, the vacuum initially drawn through the spout 34 reappears as the ethylene oxide diffuses out of the liner bag 32, giving the liner bag 32 a finished and a characteristic vacuum-tight appearance of a sterile package. A sterilizing system of the type shown in FIGS. 4 and 5 is disclosed in U.S. Pat. Nos. 3,516,223 and 3,630,665, the entire contents of which are incorporated herein by reference.

As with the system of FIGS. 1 to 3, the operator of the system of FIGS. 4 and 5 is admonished not to attempt to sterilize unless the ambient relative humidity is at least 30%. Unlike the system of FIGS. 1 to 3, whose sterilization cycle is carried out at ambient temperature, the package in the system of FIGS. 4 and 5 is placed in a heated aerator which raises the temperature of the package and causes the relative humidity in the package to fall approximately 50% for each 10 degrees rise in temperature. For example, a product packaged under ambient conditions of 30% relative humidity at 20° C. will have its relative humidity reduced to about 46 at 50° C.

Fortunately for the efficacy of the FIGS. 4 and 5 system, there is considerable inertia in the system itself such that it takes at least an hour for the package to reach its final temperature. During this time, the ethylene oxide injected directly into the package has time to kill the enclosed microorganisms Nevertheless, the physics of the system leave much to be desired.

SUMMARY OF THE INVENTION

An object of the present invention is to provide a method for assuring the maintenance of hydration of the contents of water-impermeable packages or bags containing instruments and supplies to be sterilized.

A further abject of the present invention is to provide a method for maintaining a suitable relative humidity in water impermeable packages or bags containing instruments and/or supplies to be gas sterilized, e.g., by ethylene oxide gas sterilization processes, independently of the ambient relative humidity of the environment surrounding the water impermeable packages or bags.

Yet another object of the present invention is to provide a method for maintaining a suitable relative humidity in water impermeable packages or bags containing instruments and/or supplies to be gas sterilized, which does not require measurement or consideration of the ambient relative humidity of the environment surrounding the water impermeable packages or bags.

These and other objects are achieved in accordance with the present invention by a method for maintaining the hydration of the contents of water-impermeable bags containing items to be gas sterilized which includes placing a moisture-releasing humidifying device in the water-impermeable liner bag used for gas sterilization along with wrapped items to be sterilized. The liner bag is subsequently sealed, and sterilizing gas released or introduced into the liner bag to effect sterilization. Water evaporates from the humidifying device and released into the sterilization liner bag. The released water vapor increases the relative humidity of the air within the liner bag. If the contents of the liner bag are subsequently heated, the released water vapor prevents the relative humidity from dropping to a level unsatisfactory for gas sterilization during the heating process. This effectively maintains the contents of the bag, including the microorganisms, in a hydrated state suitable for effecting gas sterilization.

DESCRIPTION OF THE PREFERRED EMBODIMENTS

Figure 6:
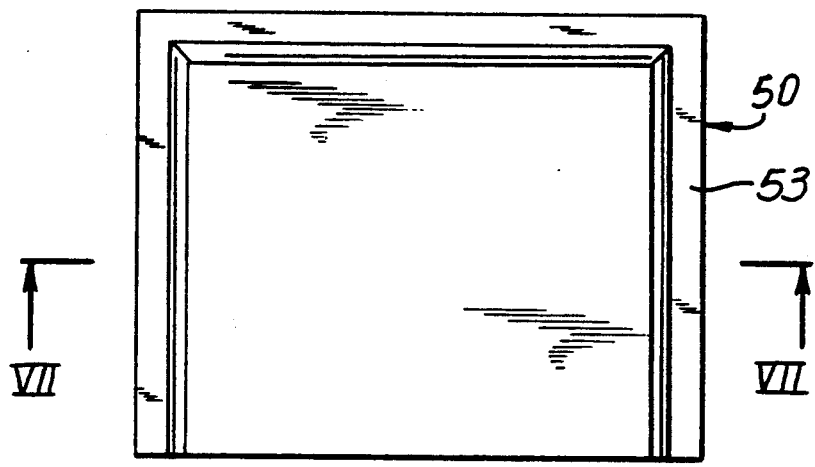
FIG. 6 is a plan view of one embodiment of a humidifying device of the present invention.
Figure 7:
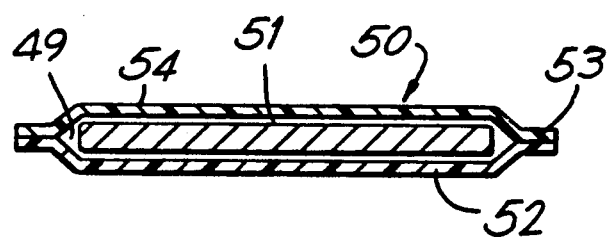
FIG. 7 is a diametric cross-sectional view of FIG. 6 taken along the line VII—VII in FIG. 6.

As shown in FIGS. 6 and 7, the humidifying device 50 of the present invention is constructed of an inner layer or wafer 51 of a water-absorbent material sandwiched and enclosed within a sealed enclosure 49 formed between outer layers 52 and 54 of a water vapor-permeable and hydrophobic material. By way of example, the wafer 51 may be approximately one inch or two inches square and may be made of a water-absorbent material having a thickness, for example, of 3/32 to ⅛ inch, and an absorbency resulting in a carrying capacity of about 500 mg of water such that the outside of the device 50 does not feel wet to the touch Wafer 51 is preferably made of paper, such as pressed paper, cardboard, blotter paper and the like, but can be constructed of other materials having the ability to absorb water. Outer layers 52 and 54 are made of a hydrophobic and water-permeable material such as spun bonded plastic fibers of polyethylene or polyolefin, an example of such material being sold by E. I. du Pont de Nemours & Co. under the trademark TYVEK. The hydrophobic but water-vapor-permeable outer layers 52 and 54 are sealed around the edges 53 to completely encase inner wafer 51 and function to prevent the damp inner wafer 51 from directly contacting items to be sterilized during the gas sterilization process. This is advantageous because many items to be sterilized might otherwise be damaged by prolonged contact with a wet surface. The wafer 51 is impregnated with water before it is sealed in the water-permeable material 52, 54. Alternatively, alcohol may be added to the water. The water-permeable material 52, 54 has interstices which provide pathways for moisture to pass out of the sealed enclosure 49. However, as previously indicated, the outside of the device 50 does not feel wet to the touch, thereby precluding undesired contact of items to be sterilized with a wet surface. Even though the device does not transmit water directly to the goods to be sterilized with which it is placed, sufficient moisture escape through the interstices of the enclosure material 52, 54 to provide the desired humidity within the enclosure in which the device 50 is placed along with the items to be sterilized, as will be further described. After the wafers 51 have been impregnated with water and sealed within the enclosure 49, the devices 50 may be stored in sealed containers, such as closed glass jars, until ready for use.

Figure 1:
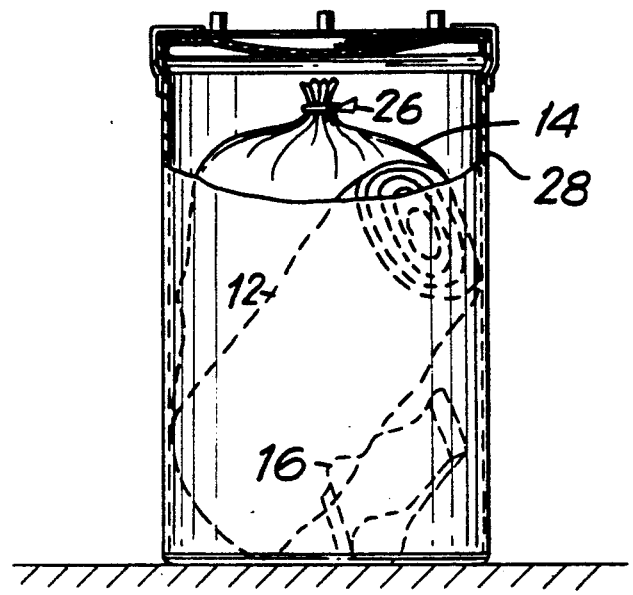
FIG. 1 is a partial sectional view of a prior art gas sterilization system.
Figure 2:
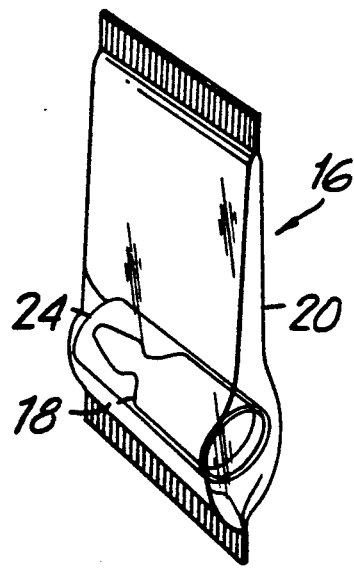
FIG. 2 is a perspective view of a prior art sterilant release mechanism for releasing sterilizing gas in the system of FIG. 1.
Figure 3:
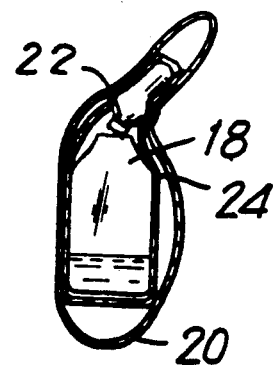
FIG. 3 is a sectional view of FIG. 2 after the sterilant has been released.
Figure 8:
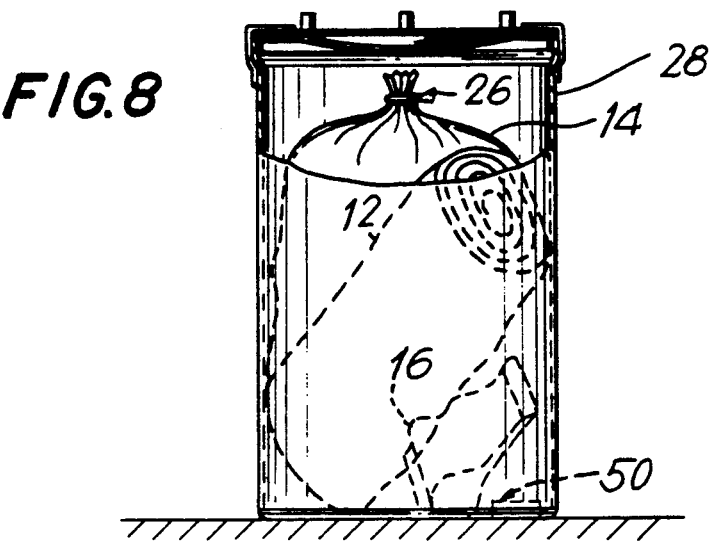
FIG. 8 is a partial sectional view showing use of the humidifying device with the gas sterilization system shown in FIG. 1.

The humidifying device of FIGS. 6 and 7 thus provides a small and inexpensive device that can be sealed into a liner bag along with the items to be sterilized when preparing items for gas sterilization. FIG. 8 shows, for example, use of the humidifying device 50 in a sterilization system of the type shown in FIGS. 1 to 3, wherein the humidifying device 50 is disposed within the liner bag 14. Thus the wrapper items 12, along with humidifying device 50 are placed in the liner bag 14, along with the activated gas release mechanism in the form of the plastic bag, and the liner bag 14 is then closed by the wire tie 26 and sterilization is effected as previously described.

Figure 9:
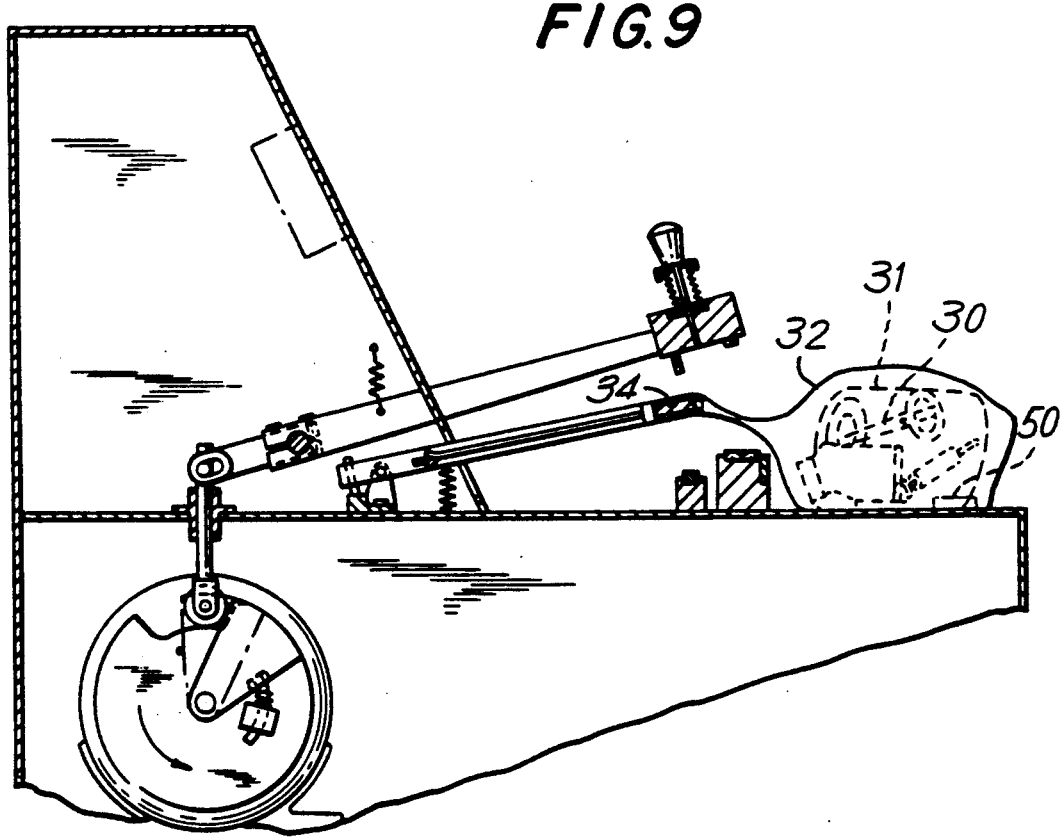
FIG. 9 is a partial sectional view showing use of the humidifying device with the sterilization system shown in FIG. 4.

In the embodiment of FIG. 9, the humidifying device 50 is placed in the liner bag 32 along with the items to be sterilized 30 which have been wrapped in paper or cloth 31. The liner bag 32 containing these items is then placed over the spout 34 and sterilization is effected as previously described. The humidifying device 50 is retained within the sealed liner bag 32 until the liner bag is eventually opened up when the contents are to be used.

In operation, the humidifying device 50 acts to maintain the requisite humidity within the respective liner bags 14 and 32 throughout the sterilization process, thereby maintaining the necessary hydration of microorganisms within the liner bag.

It is well-known that a liter of air at 20° C. which is saturated with water (100% relative humidity) contains approximately 17 mg of water. At 30° C., a liter of saturated air contains approximately 32 mg of water, at 40° C. it contains approximately 60 mg of water, and at 50° it contains approximately 100 mg of water.

When placed in a water-impermeable plastic sterilization liner bag, such as shown in FIGS. 8 and 9, the humidifying device 50 containing approximately 500 mg of water, will add about 1% relative humidity to the liner bag per minute of exposure up to about 80% relative humidity. Thereafter, humidification proceeds at a slower rate until 100% relative humidity is achieved. Moreover, one humidifying device 50 will bring the relative humidity of a five-liter plastic liner bag to 50%, even if the initial humidity within the sealed liner bag is 0%. Further, at 20° C., a single humidifying device 50 carrying about 500 mg of water is capable of fully humidifying (100% relative humidity) 29.4 liters of dry air.

It is preferred that the humidifying device 50 be capable of absorbing and carrying approximately 500 mg of water, wherein it is damp but not wet to the touch. Further, it is preferred that the device 50 actually be provided with about 500 mg of water before use. This results in a humidifying device 50 which is able to achieve the objective of the invention for virtually all known ethylene oxide gas sterilization techniques. However, the size of the device 50 and its water absorption capacity are variable. For example, a humidifying device having a water absorption capacity of 250 mg can be employed. If needed, two or more of such devices 50 can be used simultaneously to provide the necessary humidifying capacity for a single liner bag.

The shape of the humidifying device is preferably square as shown in the drawings However, other shapes such as a circular, oval, rectangular, etc. may be used, as long as the shape permits easy insertion into gas sterilization liner bags.

In operation, as shown in FIGS. 8 and 9, a humidifying device 50 is placed inside the water-impermeable plastic liner bag 14 or 32 along with wrapped items to be sterilized. In the FIG. 8 arrangement, the liner bag 14 is subsequently hermetically sealed by the tie 26, but before the items to be sterilized 12 are exposed to the ethylene oxide gas, water may be allowed to evaporate from the device 50 through the hydrophobic and water vapor-permeable outer layers 52 and 54 into the liner bag 14 to raise the relative humidity to the required level. Gas release is then effected as previously described.

Figure 4:
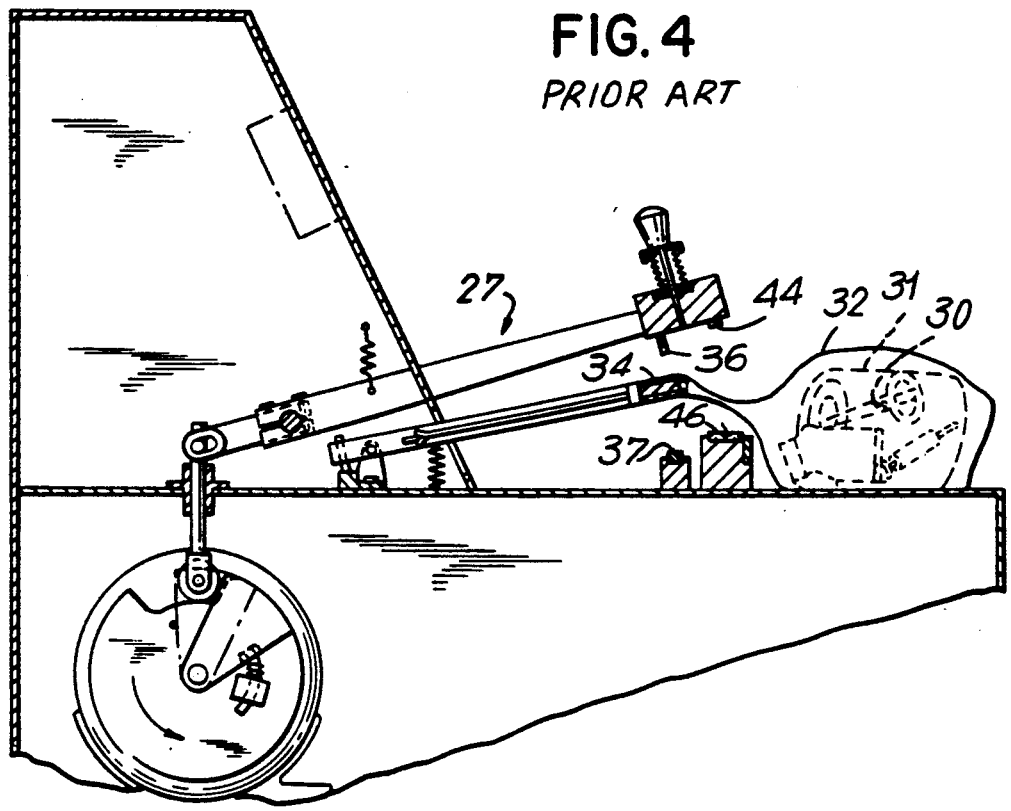
FIG. 4 is a sectional view of another prior art gas sterilization system.
Figure 5:
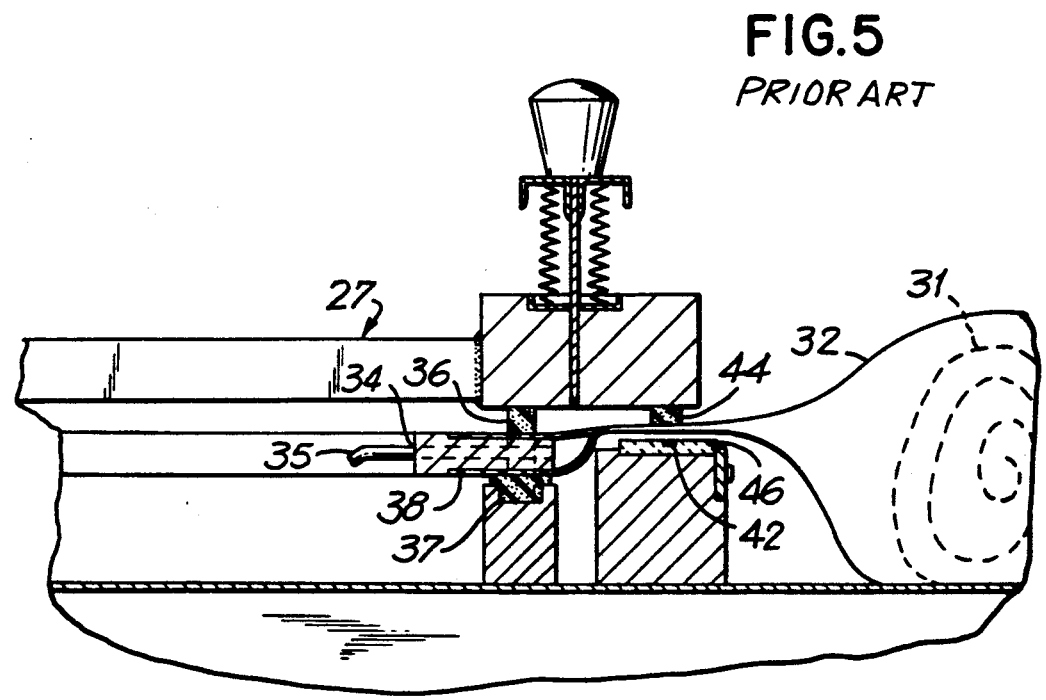
FIG. 5 is an enlarged sectional view of FIG. 4 showing another mode of operation.

If the gas sterilization technique involves subsequent heating of the contents of the liner bag as in the sterilization system of FIGS. 4 and 5, water will continue to evaporate from the humidifying device 50 during the heating to maintain the relative humidity in the liner bag 32 at or above the required level.

It is also within the scope of the invention to release or introduce ethylene oxide into the liner bag immediately following placement of the humidifying device within the liner bag.

The humidifying device of the present invention can thus be used in gas sterilization processes, such as the ethylene oxide processes disclosed in U.S. Pat. Nos. 3,476,506, 3,516,223 and 3,630,655, the entire contents of all of which are herein incorporated by reference. The humidifying device is placed in the liner bag substantially at the same time as the items to be sterilized and, either before or during the introduction or release of the ethylene oxide within the liner bag, water evaporates from the device to humidify the air in the liner bag. The remaining sterilization steps are as previously described.

There is thus provided a humidifying device and method for controlling and maintaining the relative humidity within a water-impermeable plastic liner bag during gas sterilization of items within the liner bag. The device and method maintain micro-organisms within the liner bag in a hydrated state suitable for efficient gas sterilization. Moreover, the method is self-correcting in that as the temperature within the water-impermeable liner bag increases, thus potentially decreasing the relative humidity, the rate at which water evaporates from the humidifying device into the liner bag increases, thus maintaining the relative humidity within the liner bag and preventing the decrease which would otherwise occur. Conversely, as the relative humidity in the liner bag increases, the rate of evaporation of water from the humidifying device decreases.

EXAMPLE

A practical experiment was conducted to test the efficacy of the humidifying device of the present invention.

I. 2 liters of air at 21.5° C. were measured in a water-impermeable liner bag of the type shown in FIGS. 4 and 5. The air was enclosed in the bag by inserting a probe from an electronic hygrometer into the neck of the bag and tightening the neck around the probe. The air temperature was maintained at room temperature, during which time the relative humidity of the air in the bag measured a constant 45% The bag and hygrometer then placed in a cabinet heated to 50° C. The relative humidity of the air in the bag dropped to 12% within 20 minutes.

II. Experiment I was repeated, except that a humidifying device 50 was enclosed in the same type of bag containing air The disk-shaped humidifying device 50 measured about 1 inch in diameter, had an inner absorbent paper layer 51 carrying about 500 mg of water absorbed therein and outer layers of hydrophobic, water vapor-permeable TYVEK plastic laminated around the paper layer. The humidifying device was damp to the touch but not wet. Despite heating of the air in a heating cabinet to a temperature of at least 50° C., the relative humidity of the air in the bag never fell below 45%. Moreover, when the bag was removed from the heated cabinet and allowed to cool to room temperature of 21.5° C., the relative humidity inside the bag rose to 100% and a faint haze of condensed water was visible on the inside walls of the bag.

What we claim is:

1. A method of controlling the humidity in a substantially water-impermeable package containing an item to be sterilized by a gaseous sterilant comprising the steps of providing a moisture-releasing humidifying device having a moisture-laden material disposed within a cover made at least partially of a moisture-permeable material, placing said moisture-releasing humidifying device into a water-impermeable package with an item to be sterilized, hermetically sealing the water-impermeable package, and passing moisture from said moisture-laden material through said moisture-permeable material of said cover into the package before the water-impermeable package is exposed to a gaseous sterilant.

2. A method according to claim 1, wherein a gaseous sterilant is injected into the water-impermeable package following the placing of said moisture-releasing humidifying device into said water-impermeable package.

3. A method of maintaining hydration of the contents of packages containing items to be sterilized by gas sterilization, comprising the steps of providing an enclosure made at least partially of a semi-permeable membrane and in which items are to be sterilized, introducing said items to be sterilized into said enclosure through an opening in said enclosure, providing a moisture-releasing humidifying device having a moisture-laden material disposed within a cover made at least partially of a moisture-permeable material, introducing through said opening in said enclosure said moisture-releasing humidifying device, releasing moisture from said moisture-releasing humidifying device into said enclosure by passing moisture from said moisture-laden material through said moisture-permeable material of said cover, closing said opening of said enclosure to thereby seal the interior of the enclosure from the surrounding atmosphere, releasing a sterilant gas within said sealed enclosure, and maintaining the seal of the interior of the sealed enclosure from the surrounding atmosphere while releasing said sterilant gas and while releasing said moisture into said sealed enclosure, whereby said released sterilant gas in said sealed enclosure sterilizes said items within said sealed enclosure while said released moisture maintains hydration of the contents of the sealed enclosure as said items are sterilized.

4. A method according to claim 3 further comprising utilizing said moisture-releasing humidifying device to maintain at least a 30% relative humidity within said sealed enclosure.

5. A method according to claim 3 further comprising subsequently heating said sealed enclosure, and continuing to release moisture from said moisture-releasing humidifying device into the interior of said sealed enclosure during said heating step.

6. A method according to claim 5 comprising maintaining at least a 30% relative humidity within said sealed enclosure during said heating step.

7. A method according to claim 3 further comprising utilizing said moisture-releasing humidifying device to gradually and continuously release moisture into said sealed enclosure while sterilization is effected by said sterilizing gas within said enclosure.

8. A method according to claim 3 further comprising releasing moisture from said moisture-releasing humidifying device into said sealed enclosure prior to the time that the sterilizing gas is released into the sealed enclosure.

9. A method of maintaining hydration of the contents of packages containing items to be sterilized by gas sterilization comprising the steps of providing an enclosure made at least partially of a sterilizing gas-permeable and water-impermeable membrane in which items are to be sterilized, introducing said items into said enclosure through an opening of said enclosure, providing a moisture-releasing humidifying device having a moisture-laden material disposed within a cover made at least partially of a moisture-permeable material, introducing said moisture-releasing humidifying device through said opening into sand enclosure, releasing moisture from said moisture-releasing humidifying device into the enclosure by passing moisture from said moisture-laden material through said moisture-permeable material of said cover, introducing a sealed container releasably containing a gaseous sterilant under pressure through said opening into said enclosure, sealing said opening of said enclosure from the surrounding atmosphere, and releasing the gaseous sterilant from said sealed container into the sealed enclosure to sterilize said items within the sealed enclosure while said released moisture maintains hydration of the contents of the sealed enclosure as said items are sterilized.

10. A method of maintaining hydration of the contents of packages containing items to be sterilized by gas sterilization comprising the steps of providing an enclosure made at least partially of a sterilizing gas-permeable and water-impermeable membrane in which items are to be sterilized and encapsulated until ready for use, introducing said items into said enclosure through an opening in said enclosure, providing a moisture-releasing humidifying device having a moisture-laden material disposed within a cover made at least partially of a moisture-permeable material, introducing said moisture-releasing humidifying device into said enclosure through said opening, releasing moisture from said moisture-releasing humidifying device into said enclosure by passing moisture from said moisture-laden material through said moisture-permeable material of said cover, introducing into said opening of said enclosure a conduit means and sealing the opening of the enclosure about said conduit means from the surrounding atmosphere, introducing a sterilant gas into said sealed enclosure through said conduit, and subsequently permanently sealing the interior of said sealed enclosure after the sterilant has been introduced, whereby said gaseous sterilant in said sealed enclosure sterilizes said items within said sealed enclosure while said released moisture maintains hydration of the contents of the sealed enclosure as said items are sterilized.

11. A method of controlling the humidity in a substantially water-impermeable package containing an item to be sterilized by a gaseous sterilant comprising the steps of providing a moisture-releasing humidifying device having a moisture means disposed in a cover made at least partially of a moisture-permeable material, placing said moisture-releasing humidifying device into a package with an item to be sterilized, hermetically sealing the package, and passing moisture from said moisture means through said moisture-permeable material of said cover into the package, whereby the moisture passing through said moisture-permeable material of said cover maintains hydration of the contents of said package as said item in said package is sterilized.

* * * * *